United States Patent [19]

Pitt et al.

[11] Patent Number: 5,298,191
[45] Date of Patent: Mar. 29, 1994

[54] NON-IONIC SURFACE ACTIVE COMPOUNDS

[75] Inventors: Alan R. Pitt, Sandridge; Ian M. Newington, Hazlemere, both of England

[73] Assignee: Eastman Kodak Company, Rochester, N.Y.

[21] Appl. No.: 945,631
[22] PCT Filed: Mar. 2, 1992
[86] PCT No.: PCT/EP92/00453
 § 371 Date: Oct. 22, 1992
 § 102(e) Date: Oct. 22, 1992
[87] PCT Pub. No.: WO92/15554
 PCT Pub. Date: Sep. 17, 1992

[30] Foreign Application Priority Data

Mar. 8, 1991 [GB] United Kingdom ............... 9104957

[51] Int. Cl.$^5$ ............... B01J 13/00; C07C 233/04
[52] U.S. Cl. ............... 252/308; 252/306; 252/310; 564/159; 564/156; 564/153; 430/449
[58] Field of Search ............... 564/159, 156, 153; 430/449; 252/306, 308, 310

[56] References Cited

U.S. PATENT DOCUMENTS 4,956,274  9/1990  Khanna et al. .................... 435/7

FOREIGN PATENT DOCUMENTS 0314425  5/1989  European Pat. Off. .
1360018  3/1964  France .

*Primary Examiner*—Richard L. Raymond
*Assistant Examiner*—Shailendra Kumar
*Attorney, Agent, or Firm*—Paul A. Leipold

[57] ABSTRACT

Non-ionic surface active compounds are provided having the formula

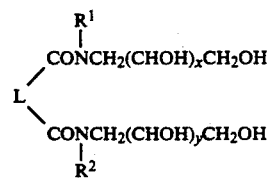

wherein L is

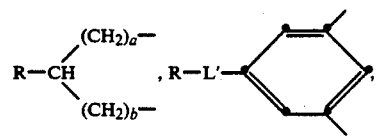

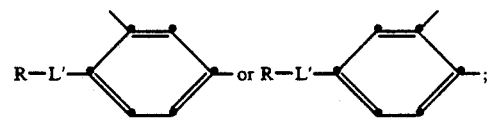

L' is a chemical bond, —O—, —S—, —NH—, —CONH— or —SO$_2$NH—;

R is a hydrophobic substituted or unsubstituted alkyl, substituted or unsubstituted cycloalkyl, or a substituted or unsubstituted aryl group;

each of R$^1$ and R$^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

They may be used as coating aids or dispersing aids in the preparation of photographic materials.

9 Claims, No Drawings

NON-IONIC SURFACE ACTIVE COMPOUNDS

The invention relates to non-ionic surface active compounds.

Non-ionic surface active compounds are known for use in a wide variety of applications. For example, they have found use as agents which lower surface tension, wetting aids and emulsifiers.

EP-A-0 314 425 describes non-ionic surface active compounds which are particularly useful as coating aids and dispersing aids in the preparation of photographic materials.

The invention provides non-ionic surface active compounds which are useful alternatives to the known compounds and which possess unexpected advantages compared to the compounds of EP-A-0 314 425.

The non-ionic surface active compounds of the invention are soluble or dispersible in water and exhibit properties that are typical of hydrophilic surfactants. For example, they lower surface tension when in solution in water and the resulting solutions readily foam and improve the wetting of hydrophobic solid surfaces. The compounds are particularly good emulsifying agents for oils. Being non-ionic, they do not cause increases in viscosity when added to charged polyelectrolyte systems e.g. aqueous gelatin. In disperse systems containing ionic surfactant and charged polyelectrolyte they can reduce viscosity, particularly at low shear.

It is often necessary to incorporate an anionic surface active agent and a non-ionic surface active agent in a hydrophilic colloid composition for photographic use. When a compound according to EP-A-0 314 425 is used in combination with an anionic surface active agent in an aqueous solution of non-deionised gelatin, an undesirable cloudiness is produced in the solution. This problem can be overcome by using a compound according to the invention instead of the surface active compound of EP-A-0 314 425.

Furthermore, the compounds of the invention are very effective at lowering the viscosity of dispersions of oils of fine droplet size in aqueous gelatin made using anionic surfactants as dispersing aids.

A further advantage possessed by the compounds of the invention is that they are more readily prepared than the compounds of EP-A-0 314 425.

The invention provides water-soluble or water-dispersible compounds having the formula $$L\begin{matrix}\diagup CONCH_2(CHOH)_xCH_2OH \\ \phantom{xxx} | \\ \phantom{xxxxx} R^1 \\ \diagdown CONCH_2(CHOH)_yCH_2OH \\ \phantom{xxx} | \\ \phantom{xxxxx} R^2\end{matrix}$$

wherein
L is

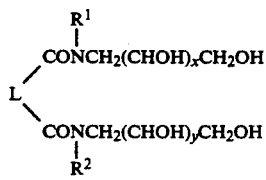

-continued

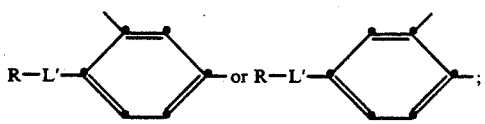

L' is a chemical bond, —O—, —S—, —NH—, —CONH— or —SO$_2$NH—;

R is a hydrophobic substituted or unsubstituted alkyl, substituted or unsubstituted cycloalkyl, or a substituted or unsubstituted aryl group;

each of R$^1$ and R$^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

Preferably, R contains from 6 to 36, more preferably from 6 to 24 and most preferably from 6 to 18 carbon atoms. A particularly preferred R group is an n-alkyl group containing from 6 to 18 carbon atoms.

Preferably, each of R$^1$ and R$^2$ independently is a methyl, ethyl, propyl or butyl group.

In accordance with another aspect of the invention there is provided a composition comprising a hydrophilic colloid and a surface active agent characterised in that the surface active agent is a compound according to the invention.

The compounds of the invention may be used as coating aids and as dispersing aids in the preparation of photographic materials.

In the preparation of a photographic material, it is usual to coat a support with one or more layers comprising an aqueous solution of a hydrophilic colloid binder, preferably, gelatin. Such layers include, for example, silver halide emulsion layers, intermediate layers, antihalation layers, filter layers, antistatic layers and protective layers. Such layers normally contain one or more surface active agents.

A number of photographic additives used in light-sensitive photographic materials are hydrophobic. Oil-soluble additives may be incorporated in the material by dissolving them in a substantially water-insoluble, high boiling point solvent which is then dispersed in an aqueous solution of the hydrophilic colloid. The formation of the dispersion may be facilitated by using an appropriate surface active agent, commonly referred to as a dispersing aid. Such oil-soluble additives include image dye-forming couplers, dye stabilizers, antioxidants and ultra-violet radiation absorbing agents. Processes for dispersing oil-soluble photographic additives are well known in the art.

The surface active agents of the invention may be used as dispersing aids. A dispersion may be formed by a process comprising dispersing a hydrophobic material in an aqueous solution of a hydrophilic colloid in the presence of a surface active agent of the invention.

When employed as a dispersing aid, the surface active agent may be used in an amount from 0.1 to 5, preferably from 0.5 to 3 percent by weight based on the weight of the dispersion.

In addition to their use as dispersing aids, surface active agents may be used as coating aids in the preparation of photographic materials. In producing the thin hydrophilic colloid layers of photographic materials, it is required that coating solutions are coated uniformly without the formation of repellency spots or craters, hereinafter referred to as repellencies. A repellency is a round, oval-shaped or comet-shaped indentation or crater in the coated layer and is usually produced by the presence of small particles or droplets of insoluble materials in the form of addenda, impurities or contaminants which are in contact with the uppermost liquid-air interface of the coated layer and are capable of reducing the surface tension of the liquid-air interface during the coating process.

A surface active agent of the invention may be used as coating aid in the preparation of a hydrophilic colloid layer. A method of making a material containing a hydrophilic colloid layer e.g. a photographic sheet material comprises coating a support with an aqueous composition comprising a hydrophilic colloid and a surface active agent of the invention.

When used as a coating aid, the surface active agent may be present in an amount from 0.01 to 1.0, preferably from 0.05 to 0.2 percent by weight based on the weight of the hydrophilic colloid coating composition.

The preferred hydrophilic colloid is gelatin e.g. alkali-treated gelatin (cattle bone or hide gelatin) and acid-treated gelatin (pigskin gelatin) or a gelatin derivative e.g. acetylated gelatin and phthalated gelatin. Other suitable hydrophilic colloids include naturally occurring substances such as proteins, protein derivatives, cellulose derivatives e.g. cellulose esters, polysaccharides e.g. dextran, gum arabic, zein, casein and pectin, collagen derivatives, agar-agar, arrowroot and albumin. Examples of suitable synthetic hydrophilic colloids include polyvinyl alcohol, acrylamide polymers, maleic acid copolymers, acrylic acid copolymers, methacrylic acid copolymers and polyalkylene oxides.

The surface active agents of the invention show good compatibility with anionic surfactants when both are incorporated in a solution of an ion-containing gelatin e.g. a solution of a regular type IV bone gelatin. This particular gelatin contains calcium ions which may be present in an amount from 3000 to 5000 ppm with respect to dry gelatin.

The hydrophilic colloid compositions of the invention are suitable for use in the preparation of photographic materials, particularly silver halide materials. Thus, in a further aspect, the invention provides a photographic material comprising a support having thereon at least one layer comprising a hydrophilic colloid composition as described above. In a preferred embodiment, the photographic material comprises a photographic silver halide emulsion layer.

In the following discussion concerning the nature of the photographic material of this invention, reference will be made to Research Disclosure, December 1978, Item 17643, published by Industrial Opportunities Ltd., The Old Harbourmaster's, 8 North Street, Emsworth, Hants P010 7DD, U. K. This publication will be identified hereafter as "Research Disclosure".

The material of this invention may comprise a negative-working or positive-working silver halide emulsion layer. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

For colour photographic materials, references giving information on couplers and on methods for their dispersions are given in Sections VII and XIV, respectively, of Research Disclosure. An account of dye-forming development is given in 'Modern Photographic Processing', Vol. 2, Grant Haist, Wiley, N.Y., 1978, Chapter 9.

The photographic materials of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic materials can be coated on a variety of supports as described in Research Disclosure Section XVII and the references described therein.

The photographic materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidize the colour developing agent. Oxidized colour developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The surface active agents of the invention may be prepared by reacting an appropriate dicarboxylic acid ester with an appropriate monosaccaride amine according to the following reaction scheme:

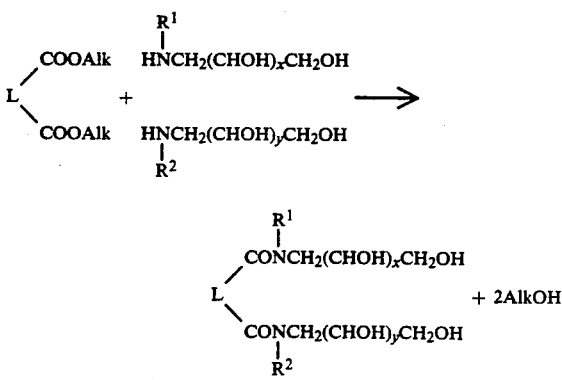

wherein L, $R^1$, $R^2$, x and y are as defined above and Alk is a lower alkyl group such as methyl.

Preferably, the reaction is carried out in the absence of a solvent. The reaction temperature may be from 140° to 200° C., more preferably from 140° to 160° C.

The dicarboxylic acid starting material may be prepared by a number of methods. One such method is shown in the following reaction scheme:

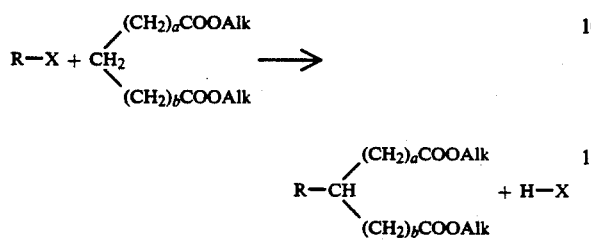

wherein X is a halogen atom, and R, Alk, a and b are as defined above. Typically, the halide starting material is reacted in solution with the dicarboxylic acid ester at an elevated temperature. Upon removal of the solvent e.g. an alkanol, water can be added and the crude product extracted into an organic solvent such as diethyl ether, dried and evaporated. The product can be purified by distillation at reduced pressure.

Another such method is shown in the following reaction scheme:

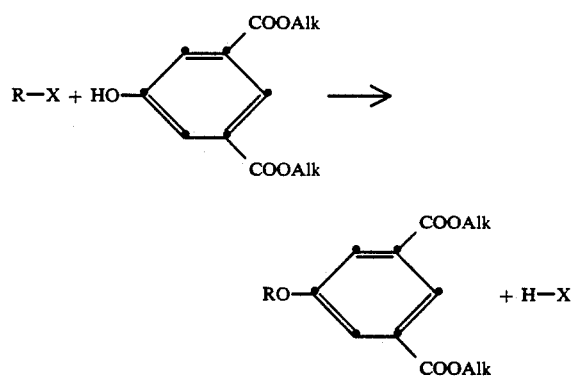

wherein X is a halogen atom, and R and Alk are as defined above. Typically, the halide starting material such as an alkyl bromide is reacted in solution with the dicarboxylic acid ester in the presence of a base such as sodium hydride. An example of a suitable solvent is dimethylformamide.

There follows a detailed description of the preparation of compounds of the invention having the following formula

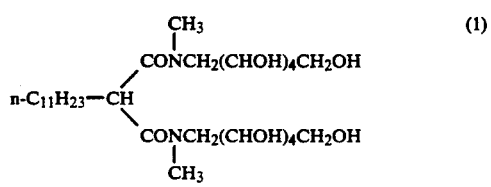

$$\underset{\substack{|\\CH_3}}{C_{12}H_{25}O}\underset{\substack{|\\CH_3}}{\overset{CONCH_2(CHOH)_4CH_2OH}{\diagup}}\overset{CONCH_2(CHOH)_4CH_2OH}{} \quad (2)$$

THE PREPARATION OF COMPOUND (1)

Two separate methods for the preparation of dodecyldimethylmalonate are given as follows:

Method 1

Sodium (4.0 g, 174 mmol) was dissolved in methanol (175 ml) and the solution heated under reflux. Dimethyl malonate (20.0 ml, 175 mmol) was added dropwise over 30 min followed by 1-bromododecane (37.5 ml, 156 mmol). Reflux was continued for 3 hours before cooling the mixture. The solvent was evaporated under reduced pressure, water (50 ml) added and the product extracted into diethyl ether (3×30 ml). The combined extracts were washed with saturated sodium chloride solution, dried (MgSO4) and evaporated. 2-Dodecyldimethyl malonate was isolated by distillation under reduced pressure as a colourless liquid (33.3 g, 71%) b.p. 136°–140° C. at 0.05 mbar. Spectroscopic data were consistent with this product.

Method 2

Dimethylmalonate (11.4 ml, 0.1 mol), dodecylaldehyde (24.0 ml, 0.11 mol), piperidine (0.4 ml, 4 mmol) and acetic acid (1.15 ml, 20 mmol) were dissolved in benzene (20 ml) and heated under reflux with azeotropic removal of water. After 5 hours the reaction was cooled and washed with water (×4) and solvent evaporated. Distillation gave 2-carboxymethylmethyltetradec-2-enoate as a pale yellow liquid (12.31 g, 41%) b.p. 145°–150° C. at 0.05 mbar.

2-Carboxymethylmethyltetradec-2-enoate (5.96 g, 20 mmol), triethylamine (4 ml, 29 mmol), 90% formic acid (0.88 ml, 22 mmol) and 10% palladium on charcoal (0.21 g, 0.2 mmol) were heated at 95°–100° C. with stirring for 24 hours. On cooling the catalyst was filtered off through Celite and washed with dichloromethane. The filtrate was washed with dilute hydrochloric acid (×3), brine, dried over magnesium sulphate and evaporated. Dodecyldimethylmalonate was isolated by distillation under vacuum in 90–98% yield. (This reduction can also be carried out with hydrogen gas, 10% palladium on charcoal in methanol).

2-Dodecyldimethylmalonate (5.0 g, 17 mmol) and N-methyl-D-glucamine (6.5 g, 34 mmol) were heated together at 140° C. for 2.5 hours under nitrogen, then for a further 2 hours under reduced pressure to remove methanol. The mixture was cooled and put under high vacuum for 12 hours to give compound (1) as a crisp solid foam.

Found: C, 55.44; H, 9.56; N, 4.38. $C_{29}H_{58}N_2O_{12}$ requires: C, 55.57; H, 9.33; N, 4.47

THE PREPARATION OF COMPOUND (2)

4-Hydroxyphthallic acid (5.0 g, 27 mmol) was dissolved in methanol (25 ml) and concentrated sulphuric acid (0.5 ml) added. The solution was refluxed for 4.5 h, cooled and the solvent evaporated. The residue was dissolved in diethyl ether (75 ml), washed with water, saturated sodium bicarbonate, brine, dried over magnesium sulphate, filtered and evaporated to give 4-hydroxydimethylphallate as a liquid which crystallized on standing (100% yield).

The above diester (4.12 g, 19.6 mmol) was added to a washed (petroleum ether) suspension of sodium hydride (0.78 g, 19.6 mmol, 60% dispersion in oil) in dry DMF (100 ml) in several portions over 15 min. After 30 min dodecyl bromide (4.89 g, 19.6 mmol) was added and the solution stirred at 20° C. for 17 h. The reaction was quenched with water (250 ml) and the resultant aqueous mixture was extracted with diethyl ether (3×100 ml). The combined ether extracts were washed with water, saturated sodium bicarbonate, brine, dried over magnesium sulphate, filtered and evaporated. 4-dodecyloxydimethylphallate was isolated by chromatography on silica gel (63–200 mesh) eluting with diethyl ether: petroleum ether (bp 40–60) 1:9, or by crystallization from ethyl acetate-petroleum ether, as a solid (4.4 g, 60%).

This reaction can also be carried out using other bases in place of sodium hydride, such as potassium t-butoxide, 1,8-diazabicyclo[5.4.0] undec-7-ene (DBU), sodium hydroxide or a sodium alkoxide. Other solvents can also be used such as tetrahydrofuran, dichloromethane or hexane (when carried out as a 2-phase reaction using a phase transfer catalyst). 1-Dodecyloxy-3,4-bis(N-methylgluconamido)benzene was prepared from 4-dodecyloxydimethylphthallate (0.54 g, 1.4 mmol) by heating under inert atmosphere with N-methylglucamine (0.56 g, 2.86 mmol) at 160° C. for 2.5 h. The reaction vessel was then evacuated (10 mm Hg) to ensure removal of all methanol, and after 1 h allowed to cool to give compound (2) as a hygroscopic solid foam.

The invention is further illustrated with reference to the following Examples in which the compounds of the invention have the formula.

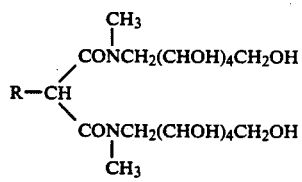

EXAMPLE 1

The surface activity of compounds of the invention was demonstrated by forming aqueous solutions of various compounds and measuring the surface tension. The results are shown in Table 1 below.

TABLE 1

| | Surface Tension mN/m in Water at 20° C. | | | |
|---|---|---|---|---|
| | Concentration in water, wt % | | | |
| R | 0.25% | 0.5% | 1.0% | 2.0% |
| n-$C_6H_{13}$ | 39.8 | 34.6 | — | — |
| n-$C_{10}H_{21}$ | 33.5 | 34.7 | 36.7 | 37.5 |
| n-$C_{12}H_{25}$ | 35.8 | 35.9 | 36.1 | 35.9 |
| n-$C_{14}H_{29}$ | 34.8 | 34.5 | 34.2 | 33.9 |
| n-$C_{16}H_{33}$ | 39.1 | 39.1 | 39.0 | 37.7 |
| n-$C_{18}H_{37}$ | 43.4 | 43.0 | 43.0 | 41.8 |

EXAMPLE 2

The use of compounds of the invention as dispersing aids in the formation of oil-in-water emulsions was demonstrated as follows.

Four of the compounds of this invention (R=n-$C_{10}H_{21}$, n-$C_{12}H_{25}$, n-$C_{14}H_{29}$ and n-$C_{16}H_{33}$) were made into 1% by weight solution in water. 10 ml aliquots of the resulting solutions were then mixed with various amounts of dodecane such that the oil:surfactant ratio was 1:1, 5:1 and 10:1. After thorough mixing with an ultrasonic microtip for 3 minutes the emulsified mixtures were left to stand. The stability of the resulting emulsions was observed. All systems had formed pinkish white dispersions due to a degree of Tyndall scattering (translucence) which suggested that the emulsions were all very finely dispersed. These emulsions were stable without significant creaming over a period of days.

EXAMPLE 3

The compatibility of compounds of the invention with an ion-containing gelatin and an anionic surfactant was demonstrated as follows.

Aqueous solutions comprising 10 percent by weight regular type IV bone gelatin containing 3000 to 5000 ppm calcium with respect to dry gelatin were formed. The solutions contained varying amounts of a commercially available anionic surfactant Alkanol XC (Dupont) which is a substituted alkyl naphthalene sulphonate. The solutions also contained varying amounts of a non-ionic surface active agent of the invention or one of the preferred non-ionic surface active agents of EP-A-O 314 425 having the formula

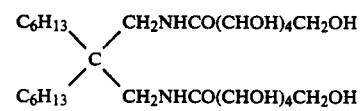

The results obtained using the surface active agent of EP-A-O 314 425 are summarised in Table 2 below.

TABLE 2

| % Alkanol XC wt/wt (soln) | % Non-ionic surface active agent wt/wt (soln) | Appearance of 10% Regular Type IV Gelatin Solution |
|---|---|---|
| 1 | 1 | Cloudy |
| 1 | 3 | Cloudy |
| 0.3 | 0.3 | Cloudy |
| 0.3 | 1 | Cloudy |
| [temperature 40° C.] | | |

An undesirable cloudy solution is obtained over a wide range of combinations of the anionic and non-ionic surfactants.

In contrast, similar experiments using compounds of the invention wherein R is n-$C_{10}H_{21}$ and R is n-$C_{12}H_{25}$, respectively, showed no cloudiness. (The compound in which R is n-$C_{12}H_{25}$ contains the same number of carbon atoms in the hydrophobic chain part of the compound as the compound of EP-A-O 314 425).

Hence, the compounds of the invention showed an advantage of compatibility in aqueous gelatin solution over the previously known surface active agent.

EXAMPLE 4

The ability of compounds of the invention to control repellencies arising from a source of surface active material within a coating composition was tested as follows.

The gelatin layers, the uppermost of which contained a compound of the invention as a coating aid, were coated onto a polyethylene terephthalate film base suitably subbed to give good adhesion to gelatin. The bottom layer consisted of a 4% by weight solution of a bone gelatin in water coated at 85.4 ml/m². The top layer consisted of a 7% by weight solution of a bone gelatin in water containing a coloured dye marker, 1 ppm oleic acid as a contaminant to indue repellency and a quantity of the surface active compound under test. The top layer was applied at a coverage of 14.2 ml/m². Both layers were applied simultaneously at a temperature of 40° C. using a conventional double slide hopper with applied suction and a linear coating speed of 15 m/min.

For each series of experiments, the coating aid was used in amounts ranging from 0.05 to 0.20% by weight based on the weight of the coating solution for the top layer.

The results are summarised in Table 3.

TABLE 3

| Concentration | Compounds (R) | | | |
|---|---|---|---|---|
| (wt %) | $n$-$C_{10}H_{21}$ | $n$-$C_{12}H_{25}$ | $n$-$C_{14}H_{29}$ | $n$-$C_{16}H_{23}$ |
| 0.05 | N | N | C* | C* |
| 0.1 | N | C | C | C |
| 0.2 | C | C | C | C |

In the above table, N denotes that the coating was covered in many repellencies while C denotes that no repellencies were produced, i.e. complete control of repellencies. C* denotes virtual control of repellencies, i.e. only occasional single repellencies were observed, of the order of one or two per meter.

Hence, the preferred compounds of this invention for coating, control repellency very effectively at low concentrations.

EXAMPLE 5

The compounds of the invention can be employed to modify the rheology of oil dispersions in aqueous gelatin containing an anionic surfactant.

Dispersions of oils of fine droplet size in aqueous gelatin made using simple anionic surfactants as dispersing aids tend to show high viscosity, particularly at low shear rates. Apprpriate levels of nonionic surfactants of the invention are very capable of reducing viscosity in such systems.

To demonstrate this, the following emulsions were prepared for rheological measurments. Each sample contained 7.5 parts didecylphthalate and 92.5 parts 7% gelatin in water+surfactant.

The surfactant content of each sample is shown in Table 4 below.

TABLE 4

| Sample | % Alkanol XC in system | % non-ionic surfactant (R = $n$-$C_{12}H_{25}$) in system |
|---|---|---|
| A | 0.7 | 1.0 |
| B | 0.7 | 0.7 |
| C | 0.7 | 0.3 |
| D | 0.7 | 0.0 |
| E | 1.0 | 0.0 |

100 ml of each sample, A-E, were heated to 50° C. in a water bath. Each sample was then premixed for 60 secs using a Polytron homogeniser (model no. PT 10-35) at maximum shear. The final emulsification was completed by running the premixed samples through a Microfluidics 'Microfluidiser' (model no. 110R) which was run at an air pressure of 4.1 bar and a water bath temperature of 50° C. Each sample was recycled round after rejecting the first 9 pumps (of piston) to remove the water in the system. The degree of recycling was fixed by limiting the number of pumps to 60. Samples were collected and viscosities were measured at 40° C. using a Bohlin VOR rheometer. The results are shown in Table 5 below.

TABLE 5

| Sample | Shear rate | | |
|---|---|---|---|
| | 10 (1/sec) | 100 (1/sec) | 1000 (1/sec) |
| A | 60 +/− 5 | 59 +/− 5 | 48 +/− 4 |
| B | 95 +/− 10 | 85 +/− 5 | 60 +/− 2 |
| C | 115 +/− 8 | 88 +/− 7 | 57 +/− 2 |
| D | 145 +/− 15 | 114 +/− 5 | 67 +/− 6 |
| E | 183 +/− 4 | 139 +/− 4 | 81 +/− 2 |

The above measurements indicate clearly that the presence of the non-ionic surfactant reduces the viscosity of the didecylphthalate/Alkanol-XC/aqueousgelatin dispersion significantly, particularly at low shear rate. It is also clear that the dispersions become less dependent on shear (i.e. more Newtonian) as the concentration of the non-ionic surfactant is increased.

We claim:

1. A water-soluble or water-dispersible compound having the formula

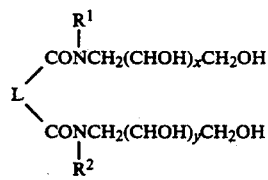

wherein
L is

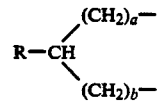

R is a hydrophobic alkyl containing 6 to 36 carbon atoms each of $R^1$ and $R^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

2. A compound according to claim 1 wherein R is an n-alkyl group containing from 6 to 18 carbon atoms.

3. A compound according to claim 1 wherein each of $R^1$ and $R^2$ independently is a methyl, ethyl, propyl or butyl group.

4. A compound according to claim 3 wherein a is 0 and b is 0.

5. A hydrophilic colloid composition containing a coating aid characterised in that the coating aid is a compound according to claim 1.

6. A hydrophilic colloid composition having dispersed therein a hydrophobic material and a dispersing aid characterised in that the dispersing aid is a compound according to claim 1.

7. A composition according to claim 5 or claim 6 wherein the hydrophilic colloid is gelatin.

8. A composition according to claim 7 wherein the gelatin is an ion-containing gelatin.

9. A composition according to claim 5 comprising an anionic surface active agent.

* * * * *